United States Patent
Chiang et al.

(10) Patent No.: US 9,950,021 B2
(45) Date of Patent: Apr. 24, 2018

(54) **ANTI-CANCER ACTIVE SUBSTANCE FROM *ANTRODIA CAMPHORATA*, METHOD FOR PREPARING THE SAME AND USE THEREOF**

(71) Applicant: National Taiwan University, Taipei (TW)

(72) Inventors: Been-Huang Chiang, Taipei (TW); Yu-Wei Lin, Taipei (TW)

(73) Assignee: National Taiwan University, Taipei (TW)

( * ) Notice: Subject to any disclaimer, the term of this patent is extended or adjusted under 35 U.S.C. 154(b) by 24 days.

(21) Appl. No.: 13/743,130

(22) Filed: Jan. 16, 2013

(65) Prior Publication Data

US 2013/0129773 A1   May 23, 2013

Related U.S. Application Data

(62) Division of application No. 12/954,112, filed on Nov. 24, 2010, now abandoned.

(30) Foreign Application Priority Data

Nov. 26, 2009 (TW) .............................. 098140278 A (51) Int. Cl.
*A61K 36/06* (2006.01)
*A61K 36/07* (2006.01)
(Continued)

(52) U.S. Cl.
CPC ............ *A61K 36/07* (2013.01); *A61K 31/341* (2013.01); *A61K 31/365* (2013.01)

(58) Field of Classification Search
CPC ...................................................... A61K 36/07

USPC ...................................................... 424/195.15
See application file for complete search history.

(56) References Cited

U.S. PATENT DOCUMENTS

| 7,109,232 | B2 | 9/2006 | Hattori et al. |
| 7,342,137 | B1 | 3/2008 | Liu et al. |

(Continued)

FOREIGN PATENT DOCUMENTS

| JP | 5752925 B2 | 7/2015 |
| WO | WO 2008/064133 | * 5/2008 |

OTHER PUBLICATIONS

Crowell et al. Molecular Cancer Therapeutics. Aug. 2003. vol. 2, pp. 815-823.*

(Continued)

*Primary Examiner* — Chris R Tate
(74) *Attorney, Agent, or Firm* — Wolf, Greenfield & Sacks, P.C.

(57) ABSTRACT

An anti-cancer active substance from *Antrodia Cinnamomea*, produced from mycelium of *Antrodia Cinnamomea* by following steps: (1) culturing mycelium of *Antrodia Cinnamomea* by liquid fermentation; (2) extracting the thus-obtained mycelium with ethanol and concentrating the extracted solution to obtain an ethanol extract; (3) dissolving the ethanol extract in water, and extracting with equal volume of ethyl acetate to obtain ethyl acetate extract; (4) purifying the ethyl acetate extract by silica gel column chromatography using hexane/ethyl acetate gradient as the mobile phase to obtain an eluate fraction g; and (5) purifying the eluate fraction g by silica gel column chromatography using hexane/ethyl acetate gradient as the mobile phase to obtain a specific eluate fraction which could be purified further to obtain the anti-cancer active substance from *Antrodia Cinnamomea*.

6 Claims, 8 Drawing Sheets

(51) Int. Cl.
*A61K 31/341* (2006.01)
*A61K 31/365* (2006.01)

(56) References Cited

U.S. PATENT DOCUMENTS

| | | | |
|---|---|---|---|
| 7,411,003 B1 | 8/2008 | Liu et al. | |
| 7,456,225 B1 | 11/2008 | Liu et al. | |
| 7,601,854 B2 | 10/2009 | Lai et al. | |
| 7,732,482 B2 | 6/2010 | Hattori et al. | |
| 7,994,158 B2 | 8/2011 | Chen et al. | |
| 2003/0113297 A1* | 6/2003 | Chen et al. | 424/93.5 |
| 2003/0148517 A1* | 8/2003 | Chen et al. | 435/383 |
| 2006/0089402 A1 | 4/2006 | Hattori et al. | |
| 2006/0099222 A1* | 5/2006 | Hattori et al. | 424/195.15 |
| 2006/0251673 A1* | 11/2006 | Hwang et al. | 424/195.15 |
| 2007/0116787 A1* | 5/2007 | Yao et al. | 424/725 |
| 2008/0103195 A1* | 5/2008 | Liu et al. | 514/464 |
| 2008/0119565 A1* | 5/2008 | Liu et al. | 514/690 |
| 2008/0261985 A1* | 10/2008 | Honda | C07C 49/743 514/239.5 |
| 2008/0312335 A1 | 12/2008 | Liu et al. | |
| 2009/0196885 A1* | 8/2009 | Yao et al. | 424/195.15 |
| 2009/0318400 A1* | 12/2009 | Chen et al. | 514/182 |
| 2010/0130584 A1 | 5/2010 | Kuo et al. | |
| 2010/0210869 A1 | 8/2010 | Wu et al. | |
| 2010/0286227 A1 | 11/2010 | Sheu et al. | |
| 2011/0009494 A1* | 1/2011 | Liu et al. | 514/690 |

OTHER PUBLICATIONS

Yang et al., Planta Med. Apr. 2009, vol. 75, pp. 512-516.
"Column chromatography", https://en.wikipedia.org/wiki/Column_chromatography, 7 pages, Sep. 22, 2015.
"Carcinogenesis", https://en.wikipedia.org/wiki/Carcinogenesis, 23 pages, Sep. 4, 2015.
Valko et al., "Free radicals, metals and antioxidants in oxidative stress-induced cancer", Chemico-Biological Interactions, 2006, pp. 1-40, vol. 160.
Burke et al., "The yin and yang of nitric oxide in cancer progression", Carcinogenesis, Jan. 25, 2013, pp. 503-512, vol. 34, No. 3.
Snyder et al., "Nitric Oxide Induces Cell Death by Regulating Anti-Apoptotic BCL-2 Family Members", PLoS One, Sep. 2009, pp. 1-14, vol. 4, Issue 9.
Furuhashi et al., "NO donor and MEK inhibitor synergistically inhibit proliferation and invasion of cancer cells", International Journal of Oncology, 2012, pp. 807-815, vol. 40.
Sugita et al., "Nitric Oxide Inhibits the Proliferation and Invasion of Pancreatic Cancer Cells through Degradation of Insulin Receptor Substrate-1 Protein", Signaling and Regulation, Jul. 27, 2010, pp. 1152-1164, vol. 8 (8).
Bingle et al., "The role of tumour-associated macrophages in tumour progression: implications for new anticancer therapies", Journal of Pathology, 2002, pp. 254-265, vol. 196.
Singh et al., "Nitric oxide: role in tumour biology and iNOS/NO-based anticancer therapies", Cancer Chemother Pharmacol, 2011, pp. 1211-1224, vol. 67.
Napoli et al., "Effects of Nitric Oxide on Cell Proliferation", Journal of the American College of Cardiology, 2013, pp. 89-95, vol. 62, No. 2.
Chang et al., "4-Acetylantroquinonol B Suppresses Tumor Growth and Metastasis of Hepatoma Cells via Blockade of Translation-Dependent Signaling Pathway and VEGF Production", J. Agric. Food Chem., 2015, pp. 208-215, vol. 63.

* cited by examiner

ANTI-CANCER ACTIVE SUBSTANCE FROM *ANTRODIA CAMPHORATA*, METHOD FOR PREPARING THE SAME AND USE THEREOF

CROSS-REFERENCE TO RELATED APPLICATIONS

This application claims priority to, and is a Divisional of, U.S. patent application Ser. No. 12/954,112, filed on Nov. 24, 2010, now pending, which claims priority from Taiwan Patent Application No. 098140278, filed on Nov. 26, 2009, both of which are hereby incorporated by reference in their entirety.

Although incorporated by reference in its entirety, no arguments or 13 disclaimers made in the parent application apply to this divisional application.

Any disclaimer that may have occurred during the prosecution of the above-referenced application(s) is hereby expressly rescinded. Consequently, the Patent Office is asked to review the new set of claims in view of all of the prior art of record and any search that the Office deems appropriate.

BACKGROUND OF THE INVENTION

1. Field of the Invention

The present invention relates to a novel anti-cancer compound identified in mycelium of *Antrodia camphorata*, the methods of cultivation, and applications of the said compound. To be more specific, the extracted compound is a bioactive anti-cancer compound that can inhibit the proliferation of hepatoma liver cancer cells and provide protection against liver cancer.

2. Description of the Prior Art

*Antrodia camphorata* is a medicinal fungus growing inside the *Cinnamomum kanchirai Hayata*, Lauraceae trunk, a native species tree found in Taiwan. *Antrodia camphorata* has been reported to have many medicinal properties including anti-oxidant, anti-inflammation, and anti-cancer properties (Chang and Chou, 2004; Mau, Huang; Huang and Chen, 2004; Song and Yen; 2003; Hseu, Chang, Hseu, Lee, Yech, and Chen, 2002; Shen, Chou, Wang, Chen, Chou, and Lu, 2004 ; Ao et al., 2009). This particular type of fungus was widely used as a treatment drug for liver-associated diseases in traditional medicine. Recently, the anti-cancer activity of *Antrodia camphorata*, particularly the anti-liver cancer activity, has attracted great interests.

Many compounds identified in *Antrodia camphorata* were demonstrated to exhibit anti-cancer activities. Lien et al. have purified 4,7-dimethoxy-5-methyl-1,3-benzodioxole from dry fruiting body of *Antrodia camphorata* and discovered that this compound can inhibit the proliferation of human colon epithelial cells (Lien et al., 2009). In addition, 24-methylenelanosta-7,9-(11)-diene-3β, 15α-diol-21-oic (MMH01), another compound identified in *Antrodia camphorata* mycelium, was shown to inhibit the growth of human leukemia cancer cells (U937) and pancreatic cancer cells (BxPC3) (Chen, Chou, and Chang, 2009). Aside from their anti-cancer activities, some compounds isolated from *Antrodia camphorata* have also displayed anti-inflammatory activities. Yang et al. (2009) purified 5 different compounds from *Antrodia camphorata* which include antroquinonol B, 4-acetyl-antroquinonol B, 2,3-(methylenedioxy)-6-methyl benzene-1,4-diol, 2,4-dimethoxy-6-methyl-benzene-1,3- diol and antrodin D, and found that they can efficiently inhibit NO production and exhibit certain anti-inflammatory effects.

Due to the high medicinal value and slow growth rate of *Antrodia camphorata*, the fruiting body of *Antrodia camphorata* is on high demand nowadays. In order to meet with the market demand of this rare fungus, many approaches have been explored and industrial-level production of *Antrodia camphorata* mycelium by using liquid culture medium has been developed (Shin, Pan, and Hsieh et al. 2006). While the medicinal effects of *Antrodia camphorata* have drawn much attention, limited studies are available in terms of identification and characterization of these bioactive anti-cancer compounds found in mycelium. Nakamura et al. discovered five derivatives of malic acid and succinic acid from mycelium of *Antrodia camphorata*, and demonstrated that these compounds have cytotoxic effects on LLC lung cancer cell line and the EC50 are between 3.6 and 20 µg/mL (Nakamure et al., 2004). Studies conducted by Cheng, Huang, Chang, Wang and Lu have suggested that polysaccharides isolated from *Antrodia camphorata* can suppress angiogenesis by down regulating the expression of cyclin D1 through inhibition of vascular endothelial growth factor receptor (VEGF receptor) signaling.

Hepatoma is the leading lethal cause of malignant cancers in China, Taiwan, Korea and south of the Sahara in Africa (Seow, Liang, Leow and Chung, 2001; Kern, Breuhahn and Schirmacher, 2002). Previous studies have shown that mycelium of *Antrodia camphorata* can protect the liver from damage caused by alcohol, CCl4 and lipopolysaccharides (Dai et al., 2003; Lu et al., 2007; Hsiao et al., 2003; Song and Yen, 2003; Hattori and Sheu, 2006; Ao et al., 2009). Guo et al. have also revealed that mycelium of *Antrodia camphorata* can reverse the liver fibrosis induced by dimethylnitrosamine, DMN (Guo et al. 2002). Moreover, in vitro study have proved that the extract of *Antrodia camphorata* mycelium can inhibit the proliferation of hepatoma liver cancer cells and the IC 50 of HepG2 and Hep3B cells are 49.5 and 62.7 µg/mL, respectively (Song, Hsu and Yen, 2005). Pan et al. cultivated the *Antrodia camphorata* using a 5-ton fermenter and have demonstrated that the extract of *Antrodia camphorata* mycelium can significantly reduce the IC50 of HepG2 hepatoma liver cancer cells to 4.25 µg/mL (Pan et al., 2008). While accumulated evidence has strongly suggested the anti-hepatoma activities of *Antrodia camphorata*, the definite bioactive anti-cancer compounds remain unclear. Therefore, to further identify and characterize the bioactive, anti-cancer compounds found in *Antrodia camphorata*, the inventor(s) have successfully 1) developed a new approach for *Antrodia camphorata* cultivation and purification, 2) identified the definite bioactive anti-cancer compound and 3) verified its use for anti-cancer treatments.

Other Reference

Ao, Z. H., Xu, Z. H., Lu, Z. M., Xu, H. Y., Zhang, X. M., and Dou, W. F. (2009). Niuchangchih (*Antrodia comphorata*) and its potential in treating liver diseases. J. Ethnopharm, 121, 194-212.

Chang, T. T., and Chou, W. N. (2004). *Antrodia cinnamomea* reconsidered and *A. salmonea* sp. nov. on *Cunninghamia konishii* in Taiwan. Botanical Bulletin Academia Sinica, 45, 347-352.

Chen, Y. J., Chou, C. J. and Chang, T. T. (2009). Compound MMH01 possesses toxicity against human leukemia and pancreatic cancer cells. Toxicology in vitro, 23, 418-424.

Cheng, J. J., Huang, N. K., Chang, T. T., Wang, D. L. and Lu, M. K. (2005). Study for anti-angiogenic activities of polysaccharides isolated from *Antrodia cinnamomea* in endothelial cells. Life Science, 76, 3029-3042.

Dai, Y. Y., Chuang, C. H., Tsai, C. C., Sio, H. M., Huang, S. C., Chen, J. C. and Hu, M. L. (2003). The protection of Antrodia camphorata against acute hepatotoxicity of alcohol in rats. Journal of Food and Drug Analysis, 11, 177-185.

Hattori, M., and Sheu, C. C. (2006). Compounds from *Antrodia camphorata* having anti-inflammatory and anti-tumor activity. U.S. Pat. No. 7,109,232.

Hseu, Y. C., Chang, W. C., Hseu, Y. T., Lee, C. Y., Yech, Y. J., and Chen, P. C. (2002). Protection of oxidative damage by aqueous extract from *Antrodia camphorata* mycelia in normal human erythrocytes. Life Science, 71, 469-482.

Hsiao, G, Shen, M. Y., Lin, K. H., Lan, M. H., Wu, L. Y., Chou, D. S., Lin, C. H., Su, C. H., and Sheu, J. R. (2003). Antioxidant and hepatoprotective effective of *Antrodia camphorata* extract. Journal of Agriculture and Food Chemistry, 51, 3302-3308.

Kern, M. A., Breuhahn, K., and Schirmacher, P. (2002). Molecular pathogenesis of human hepatocellular carcinoma. Advances in Cancer Research, 86, 67-112.

Guo, S. Q. (2002). Ameliorative effects of Antrodia camphorata on liver fibrosis and gastrointestinal functions in rats. Master Thesis. China Medical College, Taiwan.

Lien, H. M., Lin, H. W., Wang, Y. J., Chen, L. C., Yang, D. Y., Lai, Y. Y., and Ho, Y. S. (2009). Inhibition of anchorage-independent proliferation and G0/G1 cell-cycle regulation in human colorectal carcinoma cells by 4,7-dimethoxy-5-methyl-1,3-benzodioxole isolated from the fruiting body of *Antrodia camphorata*. Evidence-Based Complementary and Alternative Medicine, (In process)

Lu, Z. M., Tao, W. Y., Zou, X. L., Fu, H. Z., Ao, Z. H. (2007). Protective effects of mycelia of *Antrodia camphorate* and *Armillariella tabescens* in submerged culture against ethanol-induced hepatic toxicity in rats. Journal of Ethnopharmcology, 110, 160-164.

Mau, J. L., Huang, P. N., Huang, S. J., and Chen, C. C. (2004). Antioxidant properties of methanolic extracts from two kinds of *Antrodia camphorata* mycelia. Food Chemistry, 86, 25-31.

Nakamure, N., Hirakawa, A., Gao, J. J., Kakuda, H., Shiro, M., Komatsu, Y., Sheu, C. C., and Hattori, M. (2004). Five new maleic and succinic acid derivatives from the mycelium of *Antrodia camphorata* and their cytotoxic effects on LLC tumor cell line. Journal of Natural Products, 67, 46-48.

Pan, J. H., Chen, Y. S., Sheen, L. Y., and Chiang, B. H. (2008). Large scale submerged fermentation of *Antrodia cinnamomea* for anti-hepatoma activity. Journal of The Science of Food and Agriculture, 88, 2223-2230

Seow, T. K., Liang, R. C., Leow, C. K., and Chung, M. C. (2001). Hepatocellular carcinoma: from bedside to proteomics. Proteomics, 10, 1249-1263.

Shen, Y. C., Chou, C. J., Wang, Y. H., Chen, C. F., Chou, Y. C., and Lu, M. K.(2004). Anti-inflammatory activity of the extracts from mycelia of *Antrodia camphorata* cultured with water-soluble fractions from five different *Cinnamomum* species. FEMS Microbiology Letters, 231, 137-143.

Shih, I. L., Pan, K., and Hsieh, C. (2006). Influence of nutritional components and oxygen supply on the mycelial growth and bioactive metabolites production in submerged culture of *Antrodia cinnamomea*. Process Biochemistry, 41, 1129-1135.

Yang, S. S., Wang, G J., Wang, S. Y., Lin, Y. Y., Kuo, Y. H., Lee, T. H., (2009). New Constituents with iNOS Inhibitory Activity from Mycelium of *Antrodia camphorata*. Planta Med 2009, 75: 1-5.

Song, T. Y., and Yen, G. C. (2003). Protective Effects of Fermented Filtrate from *Antrodia camphorata* in Submerged Culture against CCl4-Induced Hepatic Toxicity in Rats. Journal of Agriculture and Food Chemistry, 51, 1571-1577.

Song, T. Y., Hsu, S. L., and Yen, G. C. (2005). Induction of apoptosis in human heptoma cells by mycelium of *Antrodia camphorata* in submerged culture. Journal of Ethnopharmacology, 100, 158-167.

Yang, S. S., Wang, G. J., Wang, S. J., Lin, Y. Y., Kuo, Y. H., and Lee, T. H. (2009). New constituents with iNOS inhibitory activity from mycelium of *Antrodia camphorata*. Planta Medica, 75, 512-516.

SUMMARY OF THE INVENTION

In one aspect, the present invention provides a novel bioactive, anti-cancer compound extracted from *Antrodia camphorata* mycelium, and said compound can inhibit the proliferation of hepatoma liver cancer cells and can protect against liver cancer.

In a further embodiment of the invention, a novel approach was developed for *Antrodia camphorata* cultivation so as to improve the extraction process of the bioactive, anti-cancer compounds.

In another aspect of the present invention, a bioactive, anti-cancer compound which can be used as a drug to treat cancer(s) is provided.

The method used to produce the bioactive anti-cancer compound from *Antrodia camphorata* comprises the following steps:

Step 1: Cultivation of the *Antrodia camphorata* by liquid fermentation;

Step 2: Extraction of the pellet of mycelium with ethanol so as to prepare the ethanol extract;

Step 3: Dissolve the ethanol extract from step 2 in water, and extract with equal volume of ethyl acetate so as to obtain the ethyl acetate extract;

Step 4: Purification of ethyl acetate extract obtained from step 3 by silica gel column chromatography using hexane/ethyl acetate gradient as the mobile phase (hexane/ethyl acetate gradient elution, ratios of hexane/ethyl acetate were from 100:0 to 0:100). At the end, 100% methanol was used to elute out final residues. Fractions collected (700 mL per fraction) were then further purified by thin-layer chromatography. Fractions f and g were eluted with 80% hexane/20% ethyl acetate to 70% hexane/30% ethyl acetate and 70% hexane/30% ethyl acetate to 60% hexane/40% ethyl acetate, respectively.

Step 5: Purification of the fraction g obtained from Step 4 by silica gel column chromatography using hexane/ethyl acetate gradient as the mobile phase (hexane/ethyl acetate gradient elution, ratios of hexane/ethyl acetate were from 80:20 to 50:50) and finally elute with 100% ethyl acetate. Collect the eluates (50 mL per fraction) which contain the fractions E, F, G, H and I. Fraction E was eluted with 80% hexane/20% ethyl acetate to 75% hexane/25% ethyl acetate, fractions F and G were in the eluate of 75% hexane/25% ethyl acetate, and fraction H and I were eluted with 75% hexane/25% ethyl acetate to 70% hexane/30% ethyl acetate, and 70% hexane/30% ethyl acetate, respectively.

Step 6: Further purification of the eluates containing fractions E, F, G, H, and I obtained from step 5 with appropriate purification methods and 4-acetylantroquinonol B was then collected.

The purification methods include, but are not limited to silica gel column chromatography. The crude ethanol extract, ethyl acetate extract, eluted fraction f, eluted fraction g, eluted fractions E, F, G, H, I and 4-acetylantroquinonol B are the bioactive anti-cancer compounds. These purified compounds can be used 1) to treat cancer directly, 2) as one of the cocktail drugs for cancer therapy, or 3) as constituents for other appropriate applications.

The bioactive anti-cancer compounds described in present invention refer to the crude ethanol extract, ethyl acetate extract, hexane/ethyl acetate extract, fraction f, fraction g, fractions E, F, G, H, I and 4-acetylantroquinonol B thereof that are prepared by the method in present invention.

In one example of the invention, the *Antrodia camphorata* (BCRC35716) were obtained from Biosources Collection and Research Center (BCRC) in the Food industry Research and Development Institute (Hsinchu, Taiwan). However, preparation of the bioactive anti-cancer compounds is not limited to this particular species.

According to the invention, the liquid fermentation refers to culturing mycelium of *Antrodia camphorata* in fermentation medium containing 2% glucose and 2% malt extract with pH adjusted to 4.5~5.0, cultured at 20-25° C., 20-100 rpm agitation and an aeration of 0.5-1 vvm in a 5-ton fermenter for 4 weeks.

In another embodiment of the invention, steps for ethanol extraction are mixing the dry mycelium with 90~99% ethanol (the ratios of mycelium to ethanol is 1:10 to 1:50 (g/mL)) and homogenized with a polytron for 12~48 hrs.

In one example of the invention, the size of the silica gel column used in step 4 is 750-75 mm, 230-400 mesh.

In another example of the invention, the size of the silica gel column used in step 5 is 420-25 mm, 230-400 mesh.

In one embodiment of the present invention, the silica gel column used in step 6 is Luna 5u Silica (2) 100 A column (4.6×250 mm) and mobile phase is the mixture of hexane/ethyl acetate in the ratio of 80 to 20.

In addition, present invention also described a bioactive anti-cancer compound which includes the effective dose of the compound and adequate diluents, excipients or carriers.

Moreover, such compound mixtures can inhibit the proliferation of cancer cells.

The present invention further identified an anti-cancer drug mixture which consists of effective dose of 4-acetylantroquinonol B and a carrier.

The present invention also provides a novel application for the above 4-acetylantroquinonol B in which the compound can be used for anti-cancer drug(s) development and such drug(s) can inhibit the proliferation of cancer cells.

The present invention will now be described more specifically with reference to the following embodiments, which are provided for the purpose of demonstration rather than limitation.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENT

The examples below are merely representative of various aspects and features of the present invention and are non-limiting. Unless defined otherwise, the materials used in present invention are all commercially available.

EXAMPLE 1

Preparation of Fermentation Broth of *Antrodia camphorata*

Source of *Antrodia camphorata*

*Antrodia camphorata* (BCRC35716) used in present invention was obtained from the Biosources Collection and Research Center (BCRC) in the Food industry Research and Development Institute (Hsinchu, Taiwan). However, extraction of the bioactive anti-cancer compounds described in present invention is not limited to this particular strain.

*Antrodia camphorata* Submerged Cultivation

Inoculate mycelium of *Antrodia camphorata* to fermentation medium containing 2% glucose and 2% malt extract with pH adjusted to 5.0 and cultured at 22° C., 50 rpm agitation and an aeration of 0.5 vvm in a 5-ton fermenter for 4 weeks.

Fermentation Broth Processing after *Antrodia camphorata* Cultivation

At the end of 4-weeks cultivation, the fermentation broth was centrifuged to separate mycelium from broth filtrate. The mycelium pellet was washed twice with distilled water to remove the trace of broth and then freeze dry and store at 4° C. For ethanol extract, dry mycelium pellet was mixed with 95% ethanol in the ratio of 1 g to 20 mL and homogenized with high-speed polytron and agitated for 24 hrs to extract the ethanol-soluble compounds. The extract was further concentrated with a rotary evaporator and stored at −80° C. for further studies.

EXAMPLE 2

Purification of the Bioactive Anti-cancer Substance from *Antrodia camphorata*

Initially, 857 g crude ethanol extract was suspended in 2 L water and then the suspension was, extracted with equal volume of ethyl acetate. The water layer was then extracted three times with water saturated n-butanol. The crude fraction, ethyl acetate fraction, n-butanol fraction and water fraction were then tested for the anti-proliferation activity toward HepG2 cells.

The fraction containing the most potent inhibitory activity was then purified by silica gel chromatography (750-75 mm, 230-400 mesh), and eluted with hexane/ethyl acetate gradient solutions (the ratios of hexane/ethyl acetate vary from 100:0 to 0:100). Finally, 100% Methanol was used to remove the trace of residues. Each fraction (700 mL) was collected and analyzed its composition pattern by thin-layer chromatography (TLC, silica gel 60 $F_{254}$, Merck Co., Darmstadt, Germany) using ethyl acetate/hexane(50/50; v/v) for development. UV 254 nm-illuminating yellow fluorescence was used to group fractions with similar skeleton. According to the analyzed results from thin-layer chromatography, 13 fractions were collected from the eluates and tested for their anti-cancer activity.

As shown in Table 1, the fraction f was obtained from hexane/ethyl acetate wash (with the ratios of hexane to ethyl acetate vary from 80/20 to 70/30) and collection tubes are at number 36 to 42 with the final volume of 4.9 L. The fraction g was obtained from hexane/ethyl acetate wash (with the ratios of hexane to ethyl acetate vary from 70/30-60/40) and collection tubes are at number 43 to 55 with the final volume of 9.1 L.

TABLE 1

The ratios of hexane/ethyl acetate of the first elution buffers

| Tube Number | Elution Buffer (mobile phase) |
|---|---|
| 1-7 | Hexane (100%) |
| 8-13 | Hexane:Ethyl acetate (98:2) |
| 14-21 | Hexane:Ethyl acetate (95:5) |
| 22-30 | Hexane:Ethyl acetate (90:10) |
| 31-40 | Hexane:Ethyl acetate (80:20) |
| 41-49 | Hexane:Ethyl acetate (70:30) |
| 50-58 | Hexane:Ethyl acetate (60:40) |
| 59-68 | Hexane:Ethyl acetate (50:50) |
| 69-78 | Hexane:Ethyl acetate (40:60) |
| 79-88 | Hexane:Ethyl acetate (30:70) |
| 89-98 | Hexane:Ethyl acetate (20:80) |
| 99-108 | Hexane:Ethyl acetate (10:90) |
| 109-120 | Ethyl acetate (100%) |
| 121-128 | Methanol (MeOH) (100%) |

The most effective anti-cancer extract is fraction g. Fraction g is eluent A in the method of purification. Collected eluent A was further purified using another silica gel column (750-75 mm, 230-400 mesh) and washed with hexane/ethyl acetate buffers (the ratios of hexane to ethyl acetate vary from 80/20 to 50/50). Pure ethyl acetate was then used for final elution and 12 fractions were collected. The eluates were collected every 50 mL and fraction E was obtained from 80/20-75/25 hexane/ethyl acetate wash and collection tubes are 44 to 56 with the final of 650 mL. Fractions F and G were obtained from the wash of 75/25 hexane/ethyl acetate, collection tubes are 57 to 61 and 62 to 69 and collected volume are 250 mL and 400 mL, respectively. Fraction H was obtained from 75/25 to 70/30 hexane/ethyl acetate wash, collection tubes are 70 to 73 and collected final volume is 200 mL. Fraction I was obtained from 70/30 hexane/ethyl acetate wash, collection tubes are 74 to 84 and collected total volume is 550 mL. All these fractions were tested for their anti-cancer activity and the most effective fraction was then further purified.

TABLE 2

The ratios of hexane/ethyl acetate of the second elution buffers

| Tube Number | Elution Buffer (mobile phase) |
|---|---|
| 1-47 | Hexane:Ethyl acetate (80:20) |
| 48-71 | Hexane:Ethyl acetate (75:25) |
| 72-97 | Hexane:Ethyl acetate (70:30) |
| 98-121 | Hexane:Ethyl acetate (65:35) |
| 122-145 | Hexane:Ethyl acetate (60:40) |
| 146-169 | Hexane:Ethyl acetate (55:45) |
| 170-191 | Hexane:Ethyl acetate (50:50) |
| 192-230 | Hexane:Ethyl acetate (100%) |

Fractions E, F, G, H, and I are collected as eluent B in the method of purification. Eluent B was further purified by using a high-performance liquid chromatography (HPLC) system equipped with a tunable absorbance detector (model 1100 series, Agilent, U.S.A.). Elution was carried out at flow rate of I mL/min with a column temperature at 25° C. and UV wavelength of 254 nm. The superlative fraction was separated by a silica column (4.6×250 mm, Luna 5u Silica (2) 100A column) with hexane/ethyl acetate (80:20, v/v) as solvent system so as to obtain the anti-cancer bioactive compound. The structure of the purified compound was further identified by nuclear magnetic resonance (NMR, Bruker AMX-400).

EXAMPLE 3

Analysis of the Inhibitory Effects of *Antrodia camphorata* Bioactive Compounds on the Hepatoma Cells Proliferation Material HepG2 cells were obtained from American Type Culture Collection, ATCC, Rockville, Md., U.S.A. and were maintained in Williams medium E (WME), containing 10 mM/L HEPES, 5 µg/mL insulin, 2 µg/mL, glucagon, 0.05 µg/mL hydrocortisone, and 5% fetal bovine serum (Gibco Life Technologies, Grand Island, N.Y., USA). Colon cancer cells (CT26, BCRC 60443), prostate cancer cells (LNCaP, BCRC 60088) and breast cancer cells (MDA-MB-231, BCRC 60425) were obtained from the Biosources Collection and Research Center (BCRC) in the Food industry Research and Development Institute (Hsinchu, Taiwan).

Method

HepG2 cells in WME were cultured on a 96-well cell culture plate (2.5×104 cells per well) and incubate at 37° C. with 5% CO2. After 4 hours incubation, replace the medium with different concentrations of *Antrodia camphorata* sample extracts. The *Antrodia camphorata* extracts were dissolved in 1% dimethyl sulfoxide (DMSO) and mixed with WME medium so as to prepare extracts at different concentrations and the final concentration of DMSO was maintained below 1%. Control cultures contained only extraction solvents, and blank wells contained 100 µL growth medium with no cells. After 72 and 96 h of incubation, cell proliferation was determined by MTS assay (MTS-based cell titer 96 non-radioactivity cell proliferation assay, Promega, Madison, Wis., U.S.A.) so as to examine the anti-hepatoma activity. MTS is a colorimetric method utilizing a tetrazolium reagent. Cell proliferation was determined at 72 and 96 h from the MTS absorbance reading at 490 nm for each concentration compared with the control. The CC50 value was determined as the cytotoxic concentration of a sample that reduced the cell viability to 50% of control in 24 h. The EC50 of a sample is defined as the median effective dose of a sample (the concentration of the sample which results in 50% of cell viability) after treating the cancer cells for a certain period of time. At least three replications of each sample were tested to confirm cell proliferation and cytotoxicity. The selective effect on cancer cells was expressed as SI (selective index) value. The SI value was determined as the ratio of CC50 versus EC50 for a tested sample.

Statistical Analysis

Statistical analysis was performed using one-way analysis of variance and Duncan's multiple-range test (SAS Institute Inc., Cary, N.C., USA) to determine significant differences among means (P<0.05).

Results

Anti-proliferative Activities of Fractions from Mycelium Crude Extract

Figure 1:
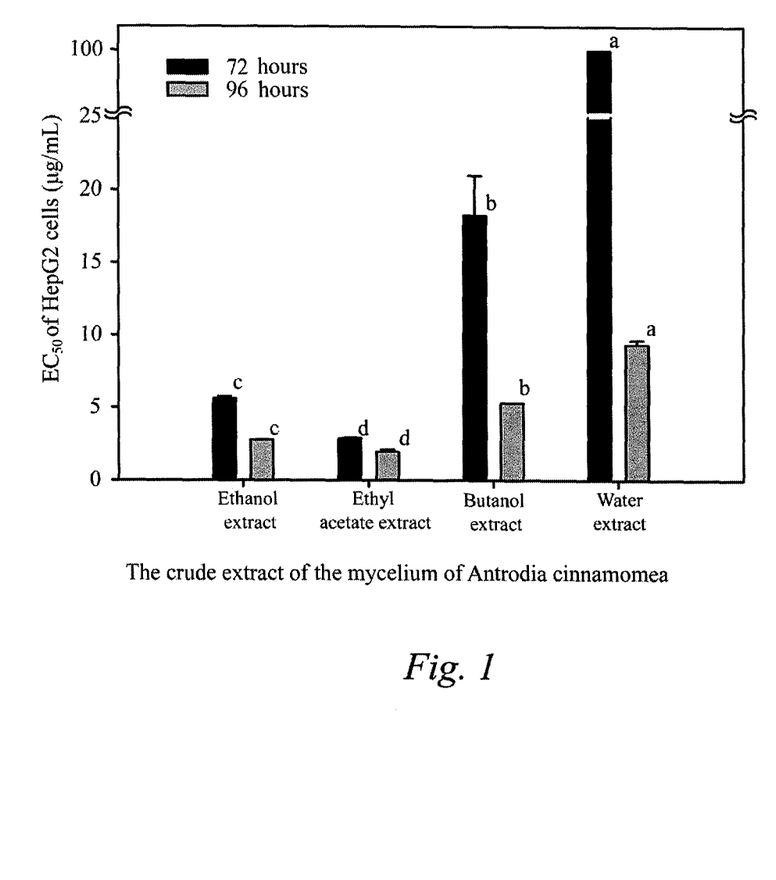
FIG. 1 shows anti-proliferative activities of fractions partitioned by various solvents. Means with different letters (a~d) within 72 and 96 hrs treatments are significantly different (P<0.05).
Figure 2A:
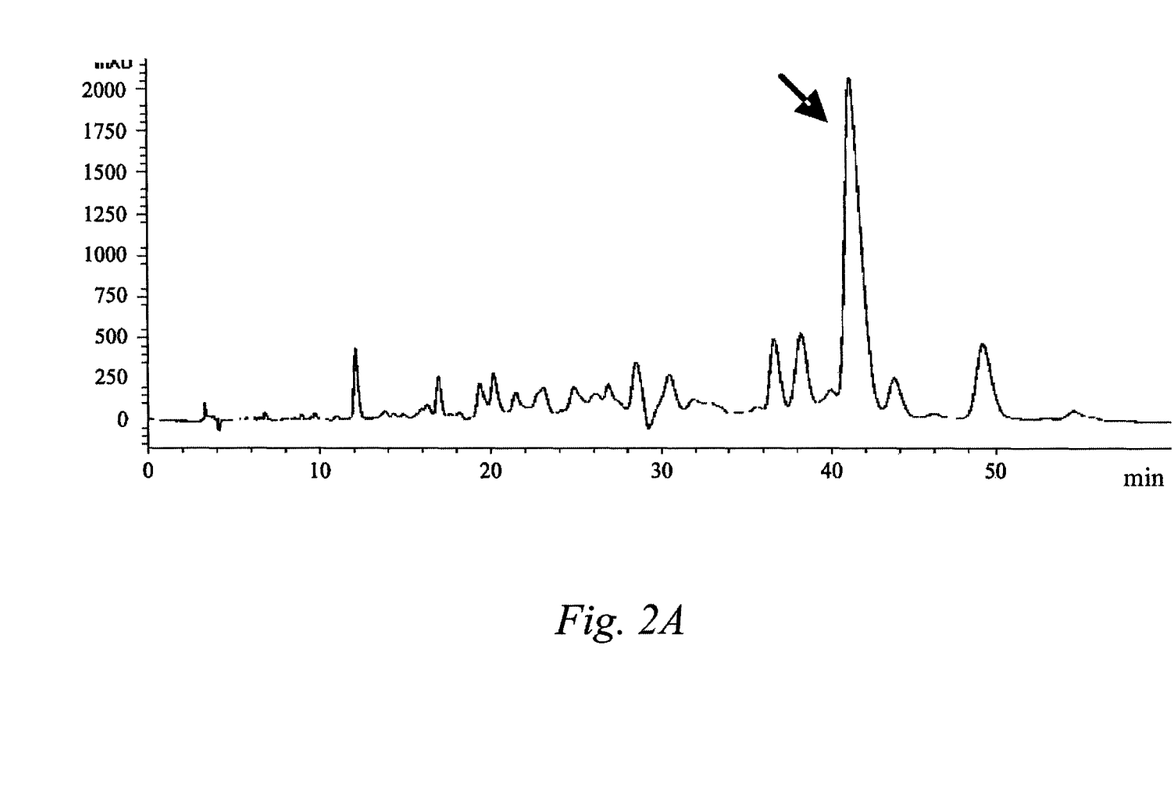
FIGS. 2A-2E show the HPLC profiles of E, F, G, H, and I fractions after the second silica gel column chromatography. 2A, 2B, 2C, 2D and 2E represent fraction E, F, G, H, and I, respectively. These fractions all contain one major peak at the same retention time as indicated by the arrows.
Figure 2B:
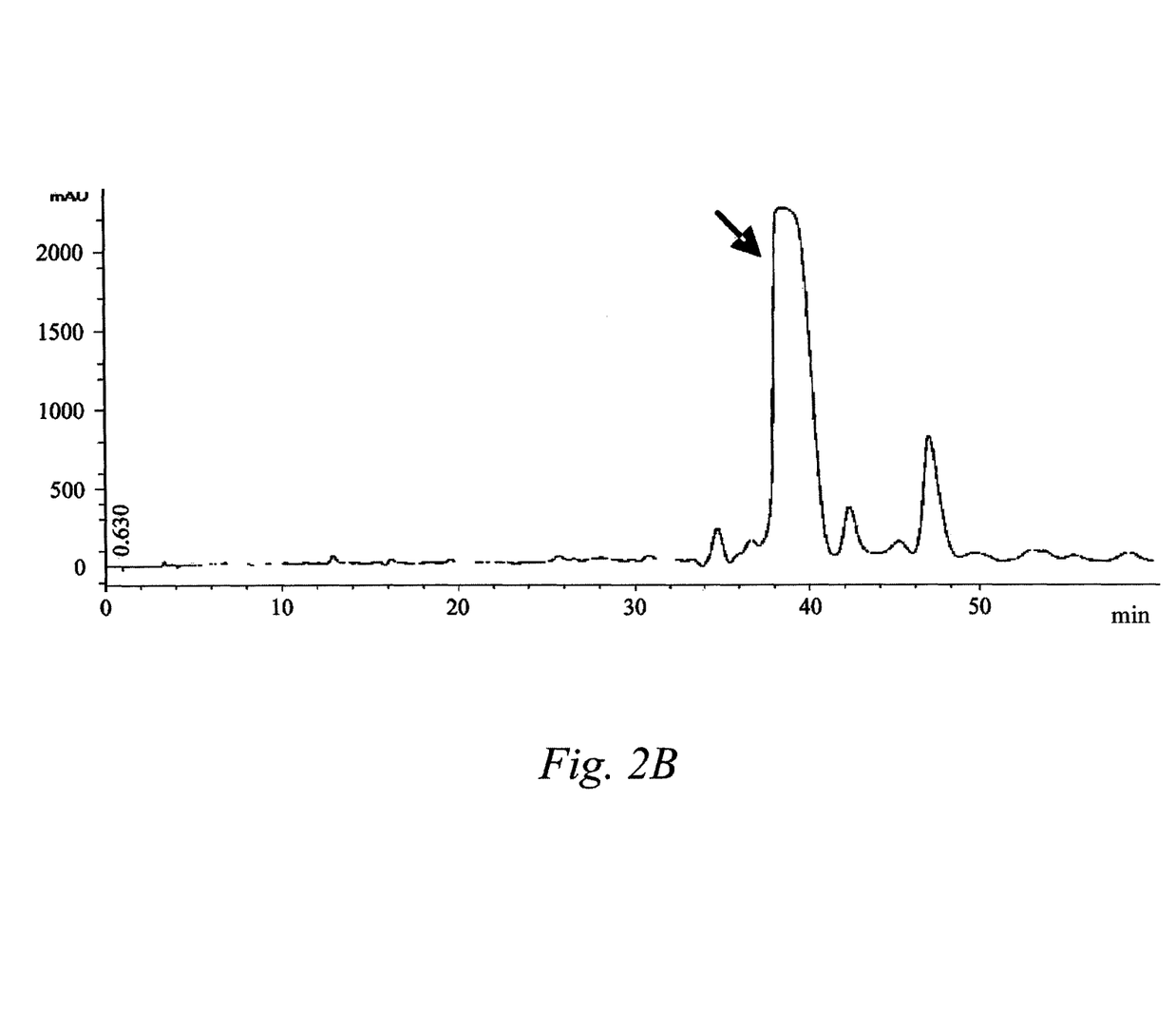
Figure 2C:
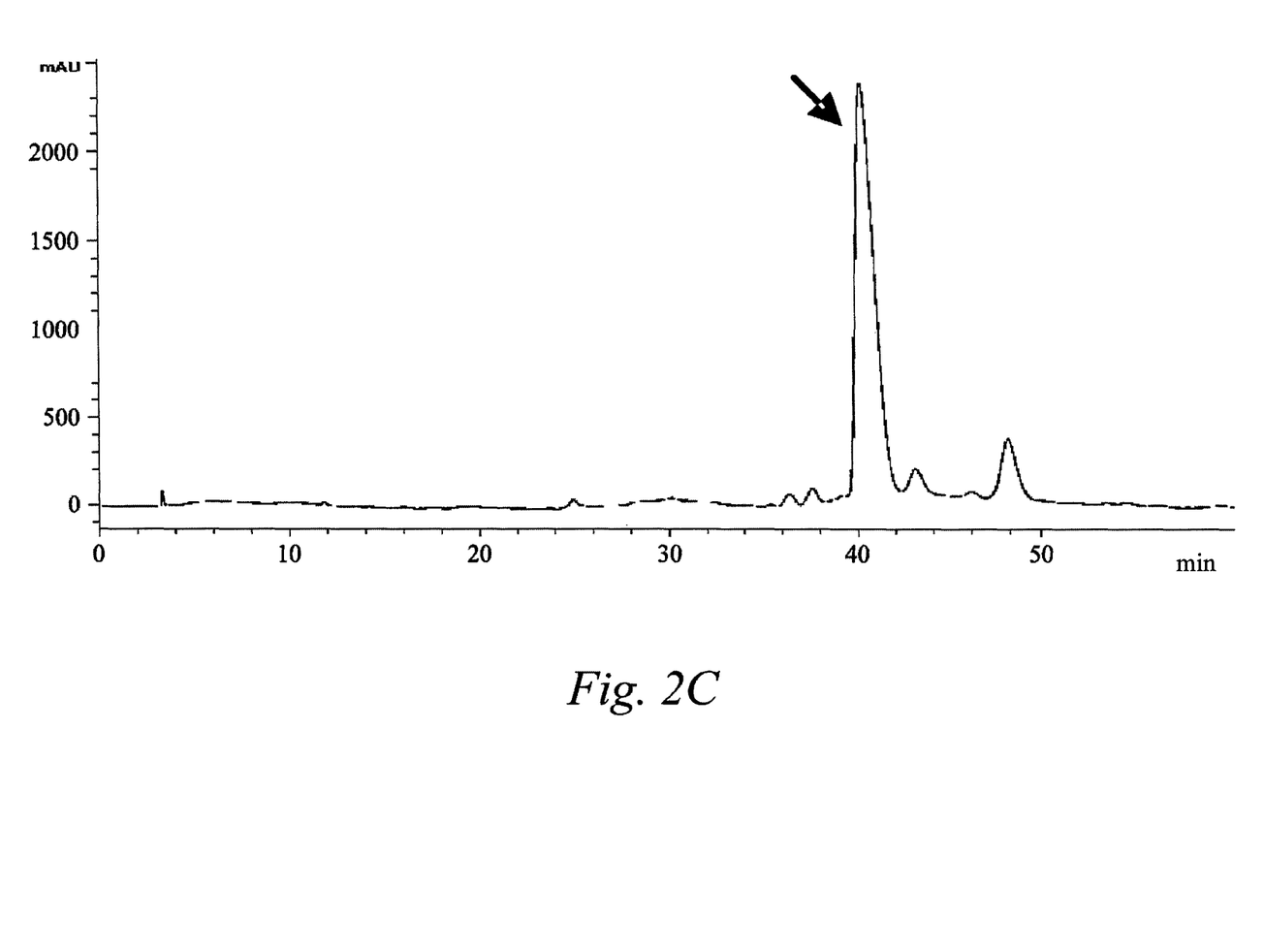
Figure 2D:
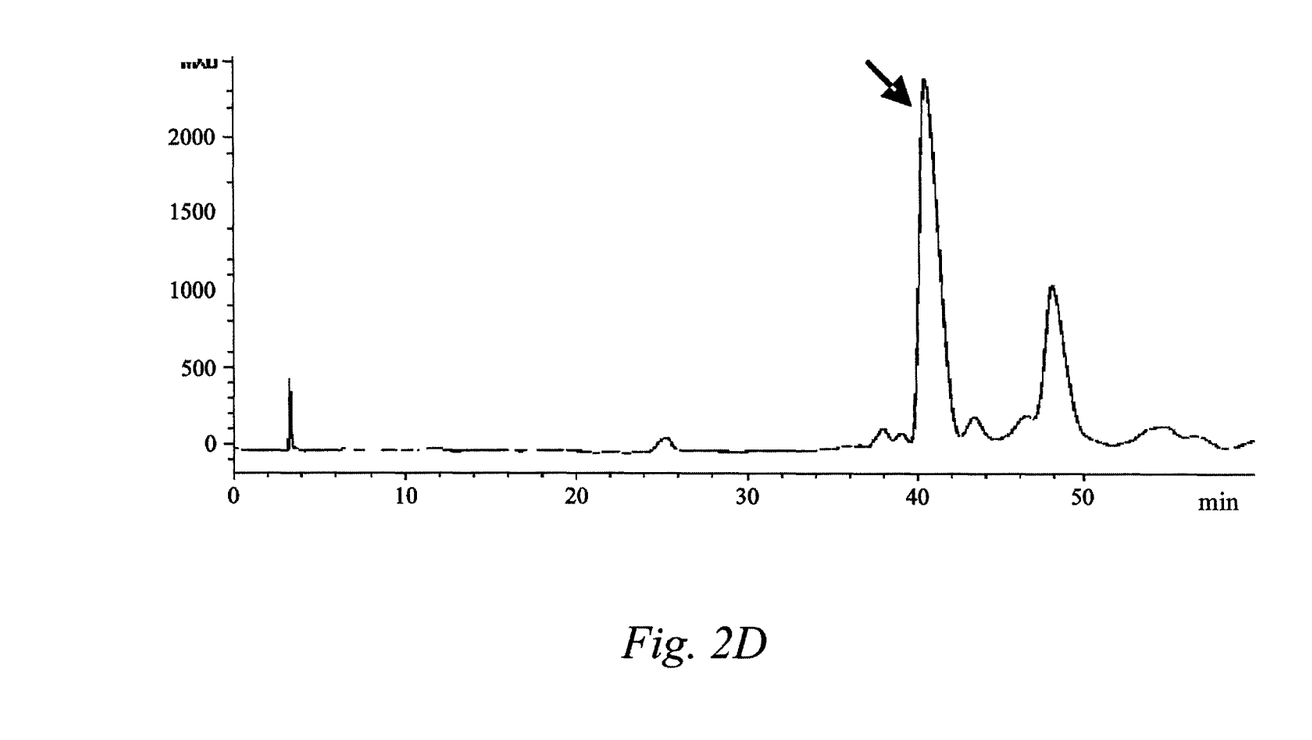
Figure 2E:
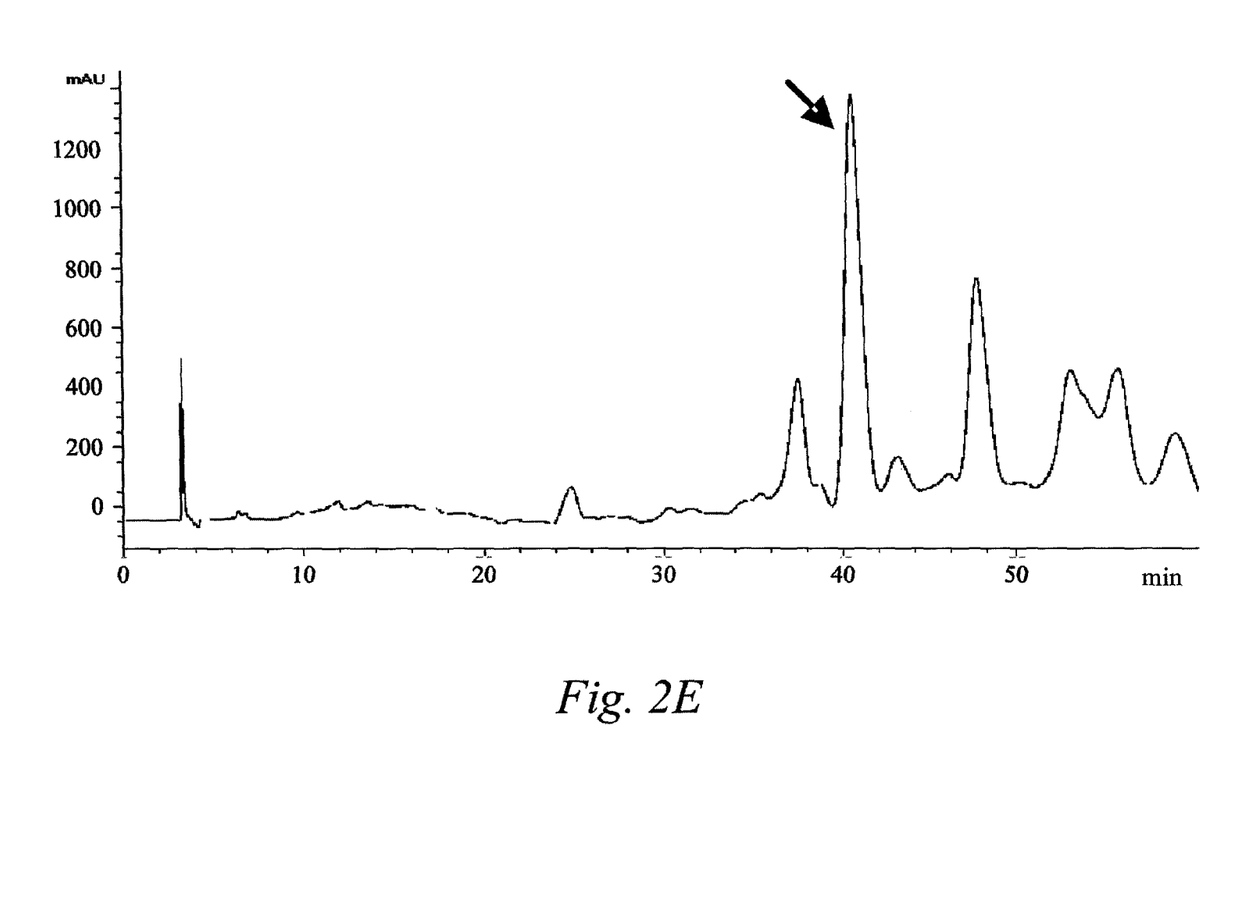

The weights of ethyl acetate fraction, n-butanol fraction, and water fraction from the ethanol extract of mycelium were 574 g, 196 g, and 87 g, respectively. Their anti-proliferative activities are shown in FIG. 1. The EC50 of crude extract, ethyl acetate fraction, n-butanol fraction and water fraction for anti-proliferation of HepG2 cells for 72 h treatment were 5.59±0.16, 2.83±0.06, 18.26±2.72, and >100 µg/mL, respectively. EC50 of these fractions for 96 h treatment were 2.76±0.01, 1.94±0.13, 5.3±0.00, and 9.35±0.32 µg/mL, respectively. It was found that the ethyl acetate fraction showed the best anti-proliferative activity among all fractions; thus this fraction was further purified by the open silica gel column.

Figure 3:
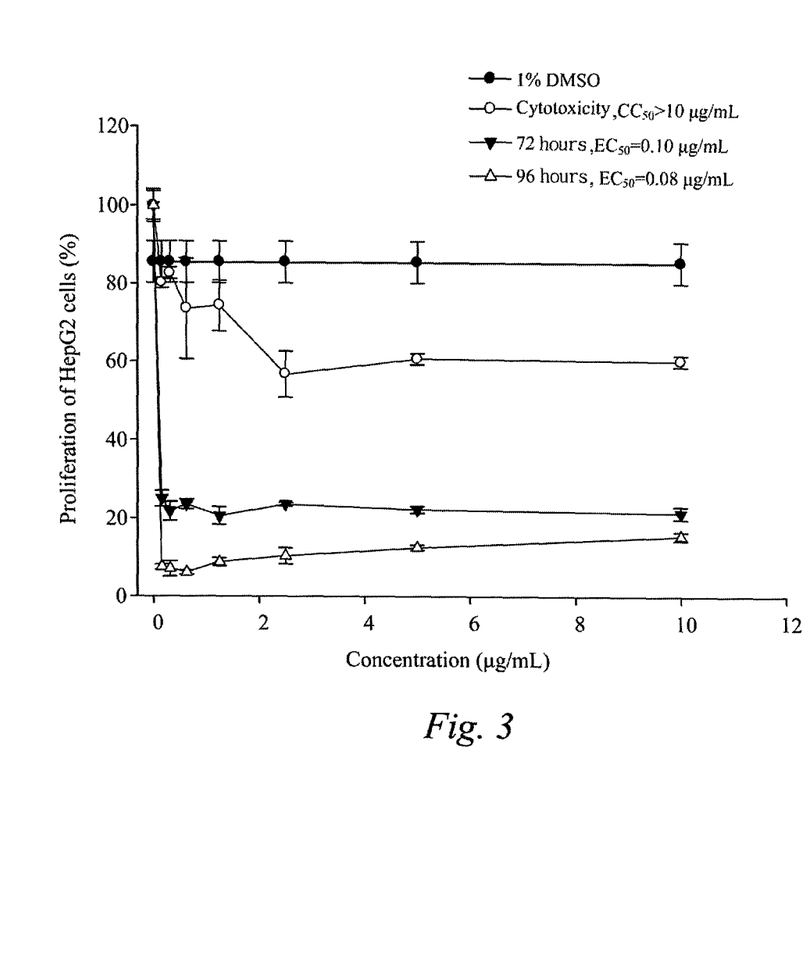
FIG. 3 shows the inhibitory and cytotoxic activity of 4-acetylantroquinonol B on the proliferation of HepG2cells.

Anti-proliferative Activities of Fractions Separated by the First Open Silica Gel Column The ethyl acetate extract was separated into 13 fractions by the open silica gel column, and the EC50 of these fractions are given in FIG. 3. Results indicated that f and g fractions had better anti-proliferative activity. However, only 2.29 g of f fraction was recovered as compared with 13.25 g recovered for g fraction. Since g fraction was the major bioactive portion quantitatively, it was used for further study.

The EC50 of g fraction toward HepG2 cells were 1.33 µg/mL and 0.82 µg/mL for 72 h and 96 h treatments, respectively. In addition, the SI value of g fraction was 86 for 96 h treatment. Due to the contaminated compounds found in g fraction based on the result of TLC, it was necessary to use an open silica gel column to further purify the bioactive compound.

TABLE 3

Cytotoxicities ($CC_{50}$) and anti-proliferative activities ($EC_{50}$) of fractions isolated from ethyl acetate by first open silica gel column against hepatoma liver cancer cells.

| Frac-tion | $CC_{50}$ (µg/mL) | HepG2 cells | | | |
|---|---|---|---|---|---|
| | | $EC_{50}$ (µg/mL) | | | |
| | | 72 hours | SI* | 96 hours | SI* |
| a | >100 | >100$^a$ | — | >100$^a$ | — |
| b | >100 | >100$^a$ | — | >100$^a$ | — |
| c | >100 | >100$^a$ | — | >100$^a$ | — |
| d | >100 | 37.04 ± 1.20$^c$ | >2.70 | 15.81 ± 1.41$^d$ | >6.33 |
| e | >100 | 13.21 ± 0.24$^f$ | >7.57 | 3.42 ± 0.21$^g$ | >29.24 |
| f | 72.75 ± 1.70 | 2.35 ± 0.17$^h$ | 30.96 | 1.59 ± 0.22$^h$ | 45.75 |
| g | 71.24 ± 3.88 | 1.33 ± 0.05$^h$ | 53.56 | 0.82 ± 0.01$^h$ | 86.88 |
| h | >100 | 8.06 ± 0.58$^g$ | >12.41 | 4.69 ± 0.26$^f$ | >21.32 |
| i | >100 | 19.81 ± 0.56$^e$ | >5.05 | 8.60 ± 0.39$^e$ | >11.63 |
| j | 73.08 ± 1.35 | 7.74 ± 1.09$^g$ | 9.44 | 3.59 ± 0.57$^g$ | 20.36 |
| k | >100 | 51.64 ± 2.20$^b$ | >1.94 | 38.92 ± 0.68$^c$ | >2.57 |
| l | >100 | 29.55 ± 4.54$^d$ | >3.38 | 22.98 ± 1.56$^c$ | >4.35 |
| m | >100 | >100$^a$ | — | >100$^a$ | — |

*Selective index (SI) = $CC_{50}/EC_{50}$.
$^{a-h}$Means with different letters within a column are significantly different (P < 0.05).

Figure 4:
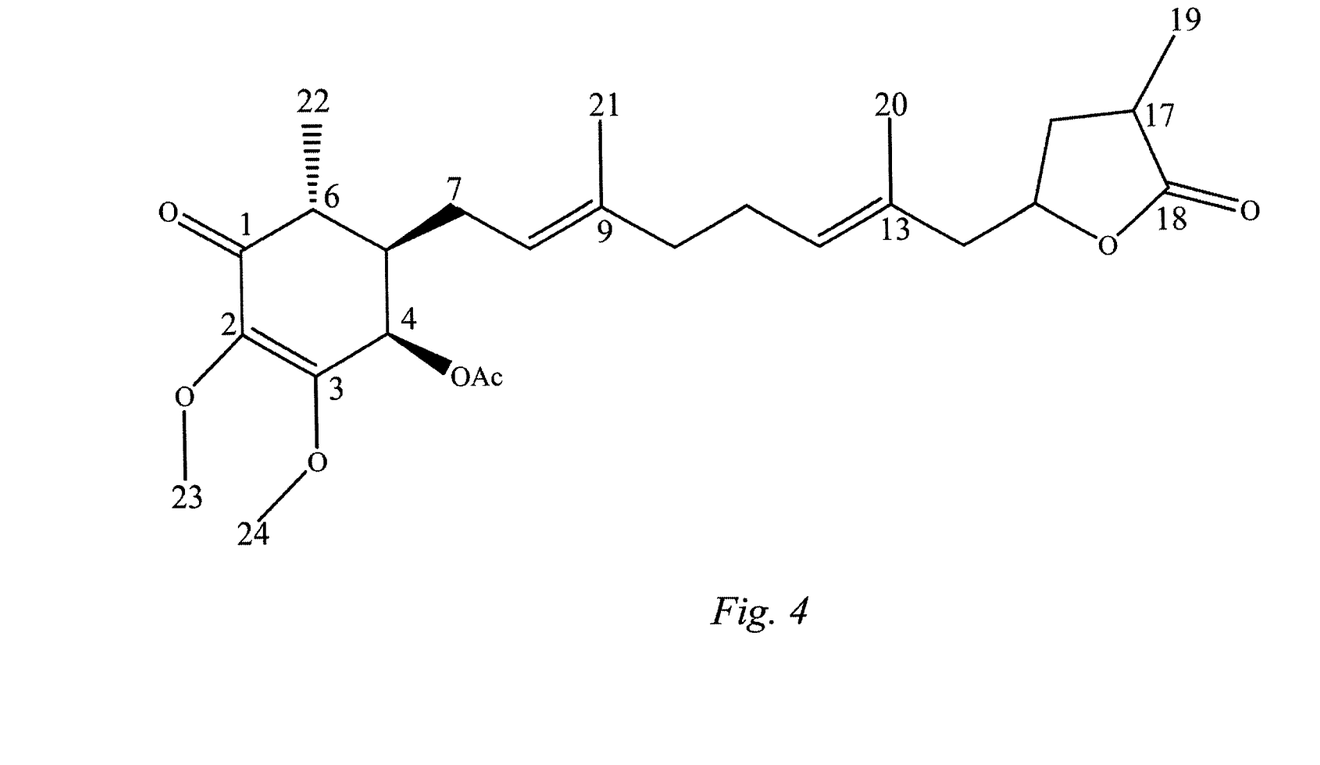
FIG. 4 shows the structure of the bioactive anti-cancer compound, 4-acetylantroquinonol B.

Anti-proliferative Activities of Fractions Separated by the Second Open Silica Gel Column Twelve fractions were isolated from the g fraction and the EC50 of these 12 fractions were shown in FIG. 4. The results indicated that fractions F, G, and H expressed better anti-proliferative activity with an EC50 of 0.5 µg/mL for 72 h treatment, and the EC50 of E, F, G, H, and I fractions were approximately 0.4 µg/mL for 96 h treatment.

After purification by the second open silica gel column, the CC50 of all fractions on HepG2 cells was >50 µg/mL. The SI values of these fractions ranged from 111 to 119 suggesting that these fractions were well-selective from hepatoma cells.

TABLE 4

Cytotoxicities ($CC_{50}$) and anti-proliferative activities ($EC_{50}$) of fractions isolated by second open silica gel column against HepG2 hepatoma liver cancer cells

| Frac-tions | $CC_{50}$ (µg/mL) | HepG2 hepatoma liver cancer cells | | | |
|---|---|---|---|---|---|
| | | $EC_{50}$ (µg/mL) | | | |
| | | 72 hours | SI* | 96 hours | SI* |
| A | >50 | >50$^a$ | — | 38.28 ± 4.45$^a$ | — |
| B | >50 | 9.94 ± 1.11$^d$ | >5.03 | 10.26 ± 0.48$^c$ | >4.87 |
| C | >50 | 15.97 ± 1.85$^c$ | >3.13 | 11.37 ± 0.07$^c$ | >4.40 |
| D | >50 | 4.74 ± 0.33$^e$ | >10.55 | 2.89 ± 0.04$^d$ | >17.30 |
| E | >50 | 0.70 ± 0.12$^g$ | >71.43 | 0.45 ± 0.01$^d$ | >111.11 |
| F | >50 | 0.50 ± 0.00$^g$ | >100 | 0.45 ± 0.01$^d$ | >111.11 |
| G | >50 | 0.57 ± 0.00$^g$ | >87.72 | 0.43 ± 0.00$^d$ | >116.28 |
| H | >50 | 0.55 ± 0.03$^g$ | >90.91 | 0.42 ± 0.01$^d$ | >119.05 |
| I | >50 | 0.68 ± 0.02$^g$ | >73.53 | 0.43 ± 0.02$^d$ | >116.28 |
| J | >50 | 3.20 ± 0.58$^f$ | >15.63 | 0.99 ± 0.17$^d$ | >50.51 |
| K | >50 | 1.29 ± 0.10$^g$ | >38.76 | 0.77 ± 0.01$^d$ | >64.94 |
| L | >50 | 20.40 ± 1.01$^b$ | >2.45 | 16.62 ± 3.42$^b$ | >3.01 |

*Selective index (SI) = $CC_{50}/EC_{50}$.
$^{a-h}$Means with different letters within a column are significantly different (P < 0.05).

Anti-proliferative Activity of Purified Fraction by HPLC

The E, F, G, H, and I fractions were further separated by HPLC and all the above fractions contain a major peak at the same retention time (FIG. 2A-E). The eluate of this major peak was collected and was tested for its bioactivity and used for further characterization. FIG. 3 shows the anti-proliferative activity of this compound. The EC50 of this compound were 0.1 and 0.08 µg/mL for 72 and 96 h treatments, respectively. This compound showed the best anti-proliferative activity among the fractions obtained throughout the entire separation process. Compared to crude extract, this compound displayed 50 times the anti-proliferative activity. The CC50 of this compound was >10 µg/mL.

Moreover, present invention also tested the anti-proliferative activity of 4-acetylantroquinonol B against other cancer cells. As shown in table 5, the IC50 of this compound against colon cancer (CT26)、prostate cancer (LNCaP) and breast cancer cells (MDA-MB-231) are 48.12±5.61、16.841±3.41 and 0.091 µg/mL, respectively, and cell viability of these tested cancer cells were below 50%. Hence, such compound can also inhibit colon、prostate and breast cancer cell growth and can be used as treatments for these cancers.

TABLE 5

The anti-proliferative activities ($IC_{50}$) of 4-acetylantroquinonol B against cancer cells

| | $IC_{50}$ (µg/mL) |
|---|---|
| colon cancer cells (CT26) | 48.12 ± 5.61 |
| prostate cancer cells (LNCaP) | 16.841 ± 3.41 |
| breast cancer cells (MDA-MB-231) | 0.091 |

Structure of the Bioactive Anti-cancer Compound

The bioactive compound was elucidated by spectroscopic methods, including 1D and 2D nuclear magnetic resonance (NMR) and mass spectral analyses. The structure is shown in FIG. 4.

4-acetylantroquinonol B electron ionization mass spectrometry: EIMS, m/z 485 [M+Na]+, 1H NMR (500 MHz, CD3OD) δ 5.73 (1H, d, J=3.0 Hz, H-4), 5.28 (1H, t, J=6.9 Hz, H-12), 5.14 (1H, t, J=6.7 Hz, H-8), 4.69 (1H, m, H-15), 3.98 (3H, s, H-24), 3.61 (3H, s, H-23), 2.74 (1H, m, H-17), 2.50 (1H, m, H-6), 2.38 (1H, dd, J=7.0, 13.8 Hz, H-14), 2.28 (2H, m, H-7), 2.27 (1H, m, H-14), 2.22 (2H, m, H-16), 2.17 (2H, m, H-11), 2.08 (3H, s, —OAc), 2.06 (2H, m, H-10), 1.93 (1H, m, H-5), 1.66 (3H, s, H-21), 1.57 (3H, s, H-20), 1.22 (3H, d, J=7.3 Hz, H-19), 1.17 (3H, d, J=6.9 Hz, H-22); 13C NMR (500 MHz, CD3OD) δ 199.0 (s, C-1), 182.7 (s, C-18), 171.4 (s, CH3CO—), 160.5 (s, C-3), 138.7 (s, C9), 138.3 (s, C-2), 131.6 (s, C-13), 129.2 (d, C-12), 122.4 (d, C-8), 78.8 (d, C-15), 70.4 (d, C-4), 61.0 (q, C-23), 60.3 (q, C-24), 45.8 (t, C-14), 44.2 (d, C-5), 42.5 (d, C-6), 40.5 (t, C-10), 35.5 (t, C-16), 35.0 (d, C-17), 27.9 (t, C-7), 27.0 (t, C-11), 20.8 (CH3CO—), 16.4 (q, C-21), 16.2 (q, C-20), 15.9 (q, C-19), 13.0 (q, C-22).

The structure of this bioactive anti-cancer compound characterized in present invention is identical to one of the five anti-inflammatory compounds, 4-acetylantroquinonol B, formerly reported by Yang et al. in 2009. However, their investigation did not expose the effects of such compound in inhibition of cancer cells growth and its applications for treating liver, colon, prostate and breast cancers (Yang et al., 2009). Thus, the present invention not only provides several bioactive anti-cancer compounds (different extracted fractions), but also novel applications of 4-acetylantroquinonol B for anti-cancer therapy. Therefore, compared with previous findings, the present invention offers advantageous methods of isolation and preparation of the bioactive compounds, and novel applications for anti-cancer therapy.

In present invention, the anti-cancer compound was purified to definite constituent and was shown to have inhibitory effects on cancer cell proliferation at very low concentrations (e.g. 0.1 µg/mL for 72 hour or 0.08 µg/mL for 96 hours). Such compound not only can be purified from *Antrodia camphorata* mycelium by liquid fermentation, but also can be produced through chemical synthesis. This novel process can significantly reduce the cost of preparation and solve the issue of high demand for scarce *Antrodia camphorata*. On the other hand, compounds obtained previously by others are crude extract and their constitutions were not determined. Such crude extract can only be obtained by extraction of fermentation broth, and that process cannot be simplified. Subsequently, the cost for preparation is expensive. Thus, the present invention provides a novel application of 4-acetylantroquinonol B which is to be used as an anti-cancer drug through its anti-proliferative activity on cancer cells.

In summary, the present invention presents an original approach for extraction of bioactive anti-cancer compounds and further identified their multifunctional properties in terms of anti-proliferative activities on cancer cells.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for inhibiting proliferation of cancer cells, comprising:
   administering an effective amount of 4-acetylantroquinonol B to a subject having cancer, wherein the cancer is hepatoma liver cancer, colon cancer, or breast cancer.

2. The method as claimed in claim 1, wherein the 4-acetylantroquinonol B is administered with a pharmaceutically diluent, an excipient or a carrier.

3. The method of claim 1, wherein the 4-acetylantroquinonol B is purified from mycelium of *Antrodia camphorate*.

4. The method of claim 1, wherein the cancer is hepatoma liver cancer.

5. The method of claim 1, wherein the cancer is colon cancer.

6. The method of claim 1, wherein the cancer is breast cancer.

* * * * *